(12) United States Patent
Hurd et al.

(10) Patent No.: US 7,201,061 B2
(45) Date of Patent: Apr. 10, 2007

(54) THREE DIMENSIONAL, REAL TIME LOAD FRAME ALIGNMENT APPARATUS AND METHOD

(75) Inventors: Milton D Hurd, Cool Valley, MI (US); Jeremy E Gaither, Warrenton, MO (US)

(73) Assignee: The Boeing Company, Chicago, IL (US)

( * ) Notice: Subject to any disclaimer, the term of this patent is extended or adjusted under 35 U.S.C. 154(b) by 63 days.

(21) Appl. No.: 11/104,043

(22) Filed: Apr. 12, 2005

(65) Prior Publication Data
US 2006/0225513 A1   Oct. 12, 2006

(51) Int. Cl.
*G01D 1/16* (2006.01)
(52) U.S. Cl. .................. 73/791; 73/789; 73/790; 73/800; 73/808; 73/821
(58) Field of Classification Search .......... 73/789, 73/790, 791
See application file for complete search history.

(56) References Cited

U.S. PATENT DOCUMENTS

| | | | | |
|---|---|---|---|---|
| 5,168,761 A * | 12/1992 | Hinant et al. | .......... | 73/791 |
| 6,148,676 A * | 11/2000 | Bergs | .......... | 73/833 |
| 6,467,356 B1 * | 10/2002 | Schoch | .......... | 73/791 |
| 6,718,833 B2 * | 4/2004 | Xie et al. | .......... | 73/812 |
| 6,983,658 B2 * | 1/2006 | Wenski | .......... | 73/800 |
| 2002/0178832 A1 * | 12/2002 | Sarabi et al. | .......... | 73/789 |
| 2004/0200293 A1 * | 10/2004 | Wenski | .......... | 73/800 |
| 2006/0010986 A1 * | 1/2006 | Wenski | .......... | 73/800 |
| 2006/0096385 A1 * | 5/2006 | Wenski | .......... | 73/800 |

* cited by examiner

*Primary Examiner*—Edward Lefkowitz
*Assistant Examiner*—Freddie Kirkland, III
(74) *Attorney, Agent, or Firm*—Harness, Dickey & Pierce, P.L.C.

(57) ABSTRACT

A system and method for assisting in real time alignment of an alignment specimen within a load frame. In one implementation an instrumented alignment specimen is used to provide information from which the deflection of the specimen at various points along the specimen can be determined. The deflection information is then used to calculate deflection values in X, Y and Z coordinate axes in real time. The deflection values are then scaled by a desired factor and then used to generate a three dimensional representation of the alignment specimen. This produces a slightly exaggerated, three dimensional representation of the alignment specimen illustrating its deformation as a result of concentric and/or angular misalignment of the lower head of the load frame relative to the upper head.

20 Claims, 6 Drawing Sheets

$X_1$ = DISTANCE FROM STATIONARY END TO FIRST SET OF STRAIN GAGES $X_2$ = DISTANCE FROM STATIONARY END TO SECOND SET OF STRAIN GAGES

Y = HALF HEIGHT OF SPECIMEN PERPENDICULAR TO BENDING PLANE

M = MOMENT APPLIED TO MOVEABLE END OF ALIGNMENT SPECIMEN

P = LOAD APPLIED TO MOVEABLE END OF ALIGNMENT SPECIMEN

ALL VALUES ARE CONSIDERED POSITIVE IN THE DIRECTION SHOWN.

THREE DIMENSIONAL, REAL TIME LOAD FRAME ALIGNMENT APPARATUS AND METHOD

FIELD OF THE INVENTION

The present invention relates to load frames used for imparting forces to test specimens, and more particularly to an apparatus and method for displaying, in three dimensional form, the forces acting on an alignment specimen being held between a movable member and a fixed member of a load frame, to more easily and accurately enable a technician to align the movable member relative to the fixed member.

BACKGROUND OF THE INVENTION

Load frames are used in a variety of applications, in particular to apply forces to a test specimen. This allows strains to be measured on the test specimen and evaluated to determine if the material of the test specimen will be suitable for an intended application. Prior to analyzing the test specimen, however, the load frame has to be checked and calibrated with an alignment specimen to ensure that the force that will be applied to the test specimen is not angularly or concentrically misaligned with an axial center of the test specimen.

Alignment of the load frame is accomplished by securing an alignment specimen between an upper head and a lower head of the load frame. The lower head is secured to a load bar which is movable linearly vertically on a pair of parallel rails. The upper head is fixed at a desired position on the load frame, and thereafter cannot move. The alignment specimen is secured at its opposite ends between the upper and lower heads. The alignment specimen typically includes a plurality of strain gages secured to it at spaced apart locations along its length. The strain gages provide indications of the bending force experienced by the alignment specimen at various points along its length as a result of the force applied to it by the lower head. If the lower head is angularly or concentrically misaligned, then the force that is applied by it will not be applied directly along the axial centerline of the alignment specimen. Thus, the alignment specimen will be subjected to bending forces at one or more point(s) along its length. An improperly aligned load frame will produce inconsistent test data when the test specimen is placed in the load frame and is subjected to a controlled force. This can lead operators to improper conclusions about the properties of the materials being tested.

Presently available load frames are typically adjusted to remove angularity and/or concentricity misalignments of the lower head relative to the upper head by collecting data from the instrumented alignment specimen. The data is then displayed on a graph to aid the operator at making alignment adjustments. Often the graph is an X-Y graph which attempts to represent the bending condition(s) at one or more points along the alignment specimen in two dimensional fashion. Since the adjustments to the load frame are made independent of each other (i.e., concentric and angular adjustments are made independently), a key problem is to determine whether the bending being experienced at a given point on the alignment specimen is due to a concentric or angular misalignment of the lower head relative to the upper head. In practice, adjustments have been made for angular and concentric misalignments by trial and error from information presented on X-Y graphs (i.e., in two dimensional fashion). This is often a time consuming process, and it typically needs to be repeated every time new test hardware is used in a load frame.

Accordingly, it would be highly desirable to provide an apparatus and method that more easily, and intuitively, allows the operator to determine and correct for angular and concentric misalignment of the lower head of a load frame relative to the upper head.

SUMMARY OF THE INVENTION

The present invention relates to an apparatus and method for more quickly and easily correcting for concentric and angular misalignment of the lower head of a load frame relative to the upper head. In one preferred implementation, an instrumented alignment specimen having a plurality of strain gages at various points along its length is secured between the lower and upper heads of the load frame. The lower head is used to apply a force to the alignment specimen while the strain gage obtains information of the strains experienced at designated points along the alignment specimen. From this information the strain measurements are normalized such that only surface strains at a plurality of points on opposing surfaces of the alignment specimen are obtained. Normalized strain information is used to obtain deflection values at the designated plurality of points on the alignment specimen. The deflection values are scaled and then used to obtain X, Y and Z axis deflection values for each designated point along the alignment specimen. The X, Y and Z-axis values are then used to generate a three dimensional visual display on a display screen. The three dimensional image of the alignment specimen provides a slightly exaggerated representation of the deformation of the alignment specimen. The three dimensional image allows the operator to more quickly and easily make adjustments to the upper head of the load frame to align it such that the force that it produces is directed precisely along the axial center of the alignment specimen. Optionally, one or more two dimensional images of the alignment specimen can also be generated on the display screen.

The method and apparatus of the present invention thus allows alignment of the lower head, relative to the upper head, of a load frame to be accomplished more quickly, easily and intuitively than would otherwise be possible with only two dimensional information presented in graphical form.

The features, functions, and advantages can be achieved independently in various embodiments of the present inventions or may be combined in yet other embodiments.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

The following description of the preferred embodiment(s) is merely exemplary in nature and is in no way intended to limit the invention, its application, or uses.

Figure 1:
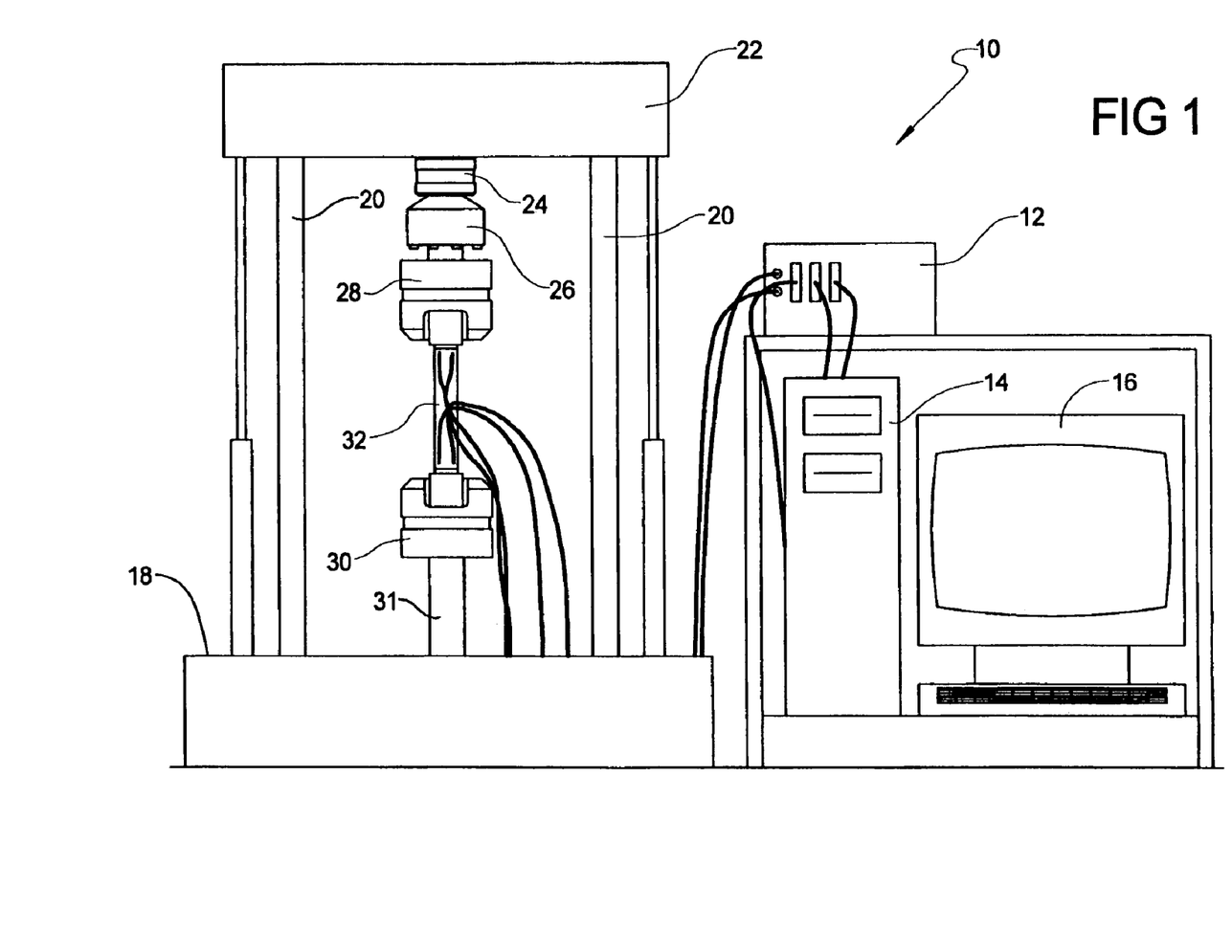
FIG. 1 is a perspective view of a conventional load frame with which the apparatus and method of the present invention is used.

Referring to FIG. 1, there is shown a conventional load frame 10 coupled to a conventional SCXI chassis 12, and a computer system 14. The computer system 14 is also coupled to a display monitor 16. The load frame 10 is a well known component that may be purchased from a variety of manufacturers. One such manufacturer is MTS Systems Corporation of Eden Prairie, Minn. The SCXI chassis 12 is commercially available from National Instruments Corporation of Austin, Tex. The computer system 14 is a conventional PC that includes an internal analog-to-digital (A/D) board in communication with an output from the SCXI chassis 12. Display 14 may be a conventional CRT or LCD panel.

The load frame 10 generally includes a hydraulic press 18, a pair of parallel, tubular guide rods 20 and a load bar 22 that is movable vertically along the guide rods 20. The load bar 22 supports an alignment fixture 24, a load cell 26 and a fixed upper head 28. The press 18 supports a movable lower head 30 from a cylindrical member 31. An instrumented alignment specimen 32 is secured at its opposite ends to the upper and lower heads 28 and 30, respectively. A linear force is applied to the alignment specimen 32 by the press 18 acting on the movable lower head 30, in response to signals generated from the computer 14 and the SCXI chassis 12. Strain information generated by the alignment specimen 32 is then fed back to the computer 14 and displayed on the monitor 16. It is a principal advantage of the present invention that the angular and concentric misalignment forces acting on the alignment specimen 32 are displayed by a three dimensional representation of the alignment specimen that highlights the deformation it experiences when the load is applied to it. This allows the operator to much more quickly, easily and intuitively apply alignments to the alignment fixture 24 via a plurality of adjustment screws (not shown) on the alignment fixture 24, such that the upper load head 28 is aligned precisely along an axial centerline of the alignment specimen 32.

Figure 2:
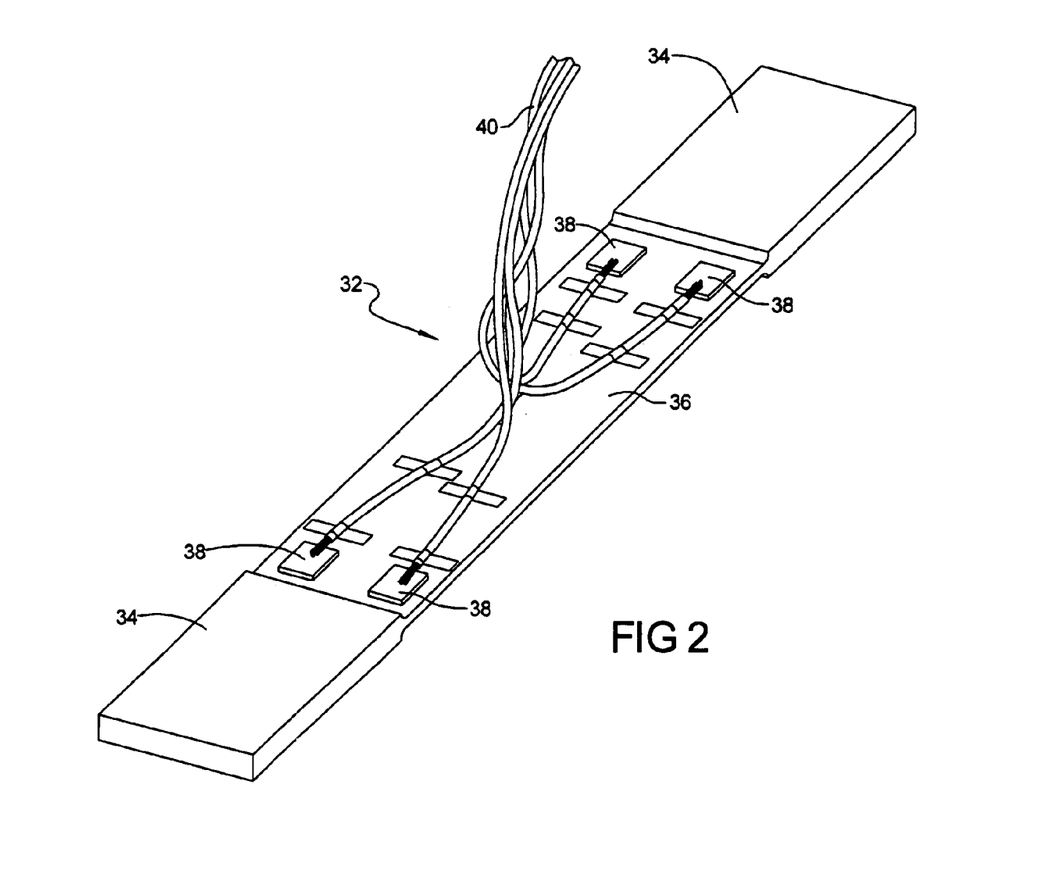
FIG. 2 is a perspective view of a typical alignment specimen incorporating a plurality of strain gages formed thereon that is used in the load frame of FIG. 1 for alignment purposes.

With brief reference to FIG. 2, the alignment specimen 32 can be seen in greater detail. The alignment specimen 32 preferably includes a pair of enlarged thickness end portions 34 separated by a central portion 36. On the central portion at a plurality of spaced apart locations are a plurality of strain gages 38. Strain gages 38 are bonded to the surface of portion 36 and coupled to a wire harness 40, that is in turn coupled to the SCXI chassis 12. In one preferred implementation eight strain gages are bonded to the central portion 36 of the alignment specimen 32, however, a greater or lesser plurality of strain gages could be employed depending upon the accuracy that one desires to achieve during the alignment procedure.

Figure 3:
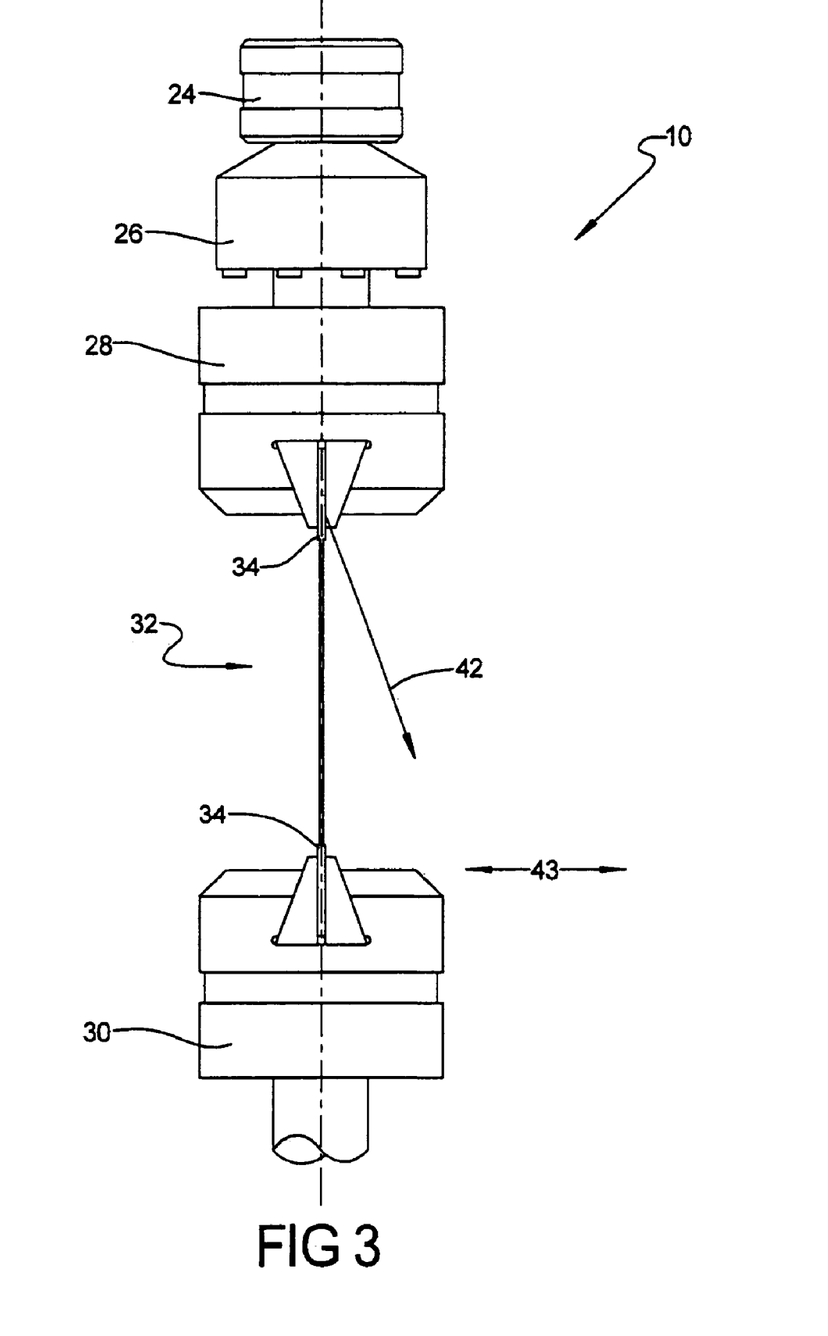
FIG. 3 is a side view of a simplified version of the alignment specimen to aid in explaining the formulas used in a preferred implementation of the present invention.

With brief reference to FIG. 3, a simplified representation of the two misalignments that need to be corrected for will be described. When the upper head 28 is precisely aligned with the lower head 30, the lower head 30 will exert an upward force precisely along the axial centerline of the alignment specimen 32. If the upper head 28 is not perfectly perpendicular to the axial centerline, then the lower head 30 will tend to exert a force at an angle 42, which is drawn extremely exaggerated in FIG. 3. This is termed "angular" misalignment. If the upper head 28 is concentrically misaligned with the axial centerline (i.e., laterally displaced from the axial centerline along axis 43), this will also cause the lower head 30 to exert a force that is not applied directly along the axial centerline of the alignment specimen 32. Accordingly, concentric and axial misalignments both need to be accounted for so that the lower head 30 is applying a force directly along the axial centerline of the alignment specimen 32. When one or both of axial or concentric misalignments are present, such misalignments influence the strain readings sensed by the instrumented alignment specimen 32. These misalignments would lead to inaccuracies in test results on an actual test specimen that is placed in the load frame 10.

Figure 4:
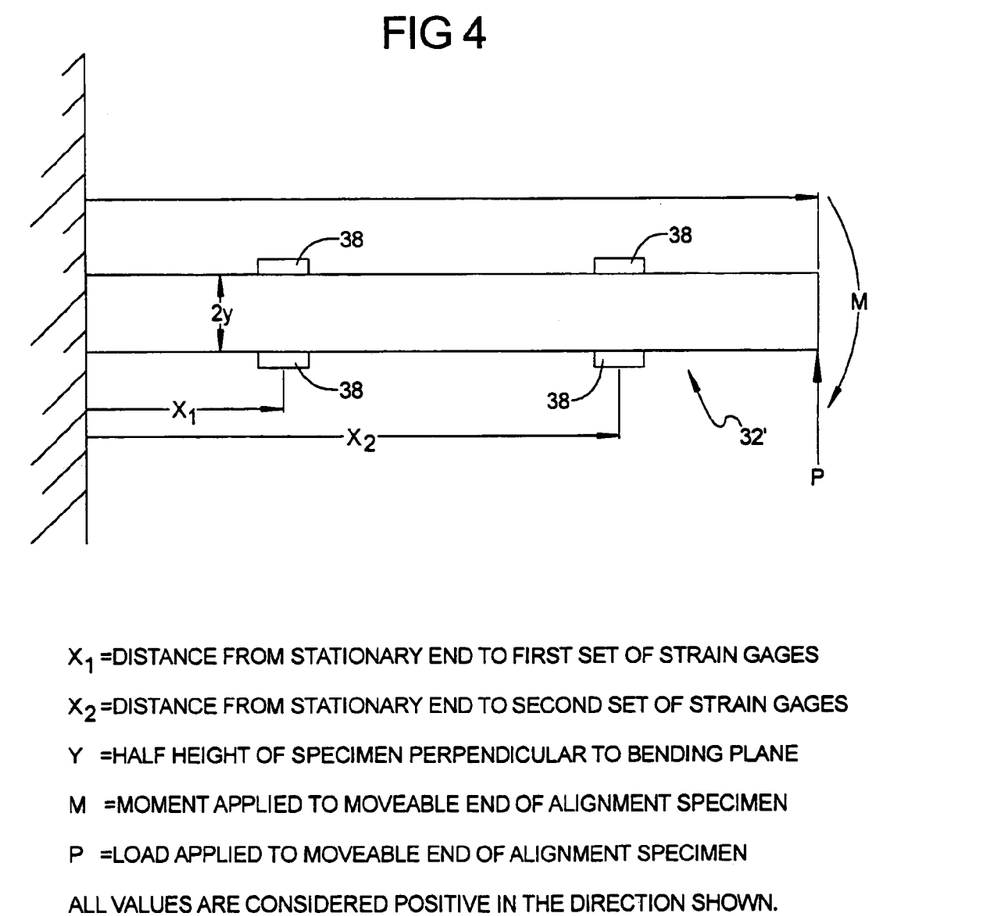
FIG. 4 is a view of the alignment specimen secured between the upper and lower load heads and illustrating a small degree of angular misalignment of the upper head relative to the lower head.
Figure 5:
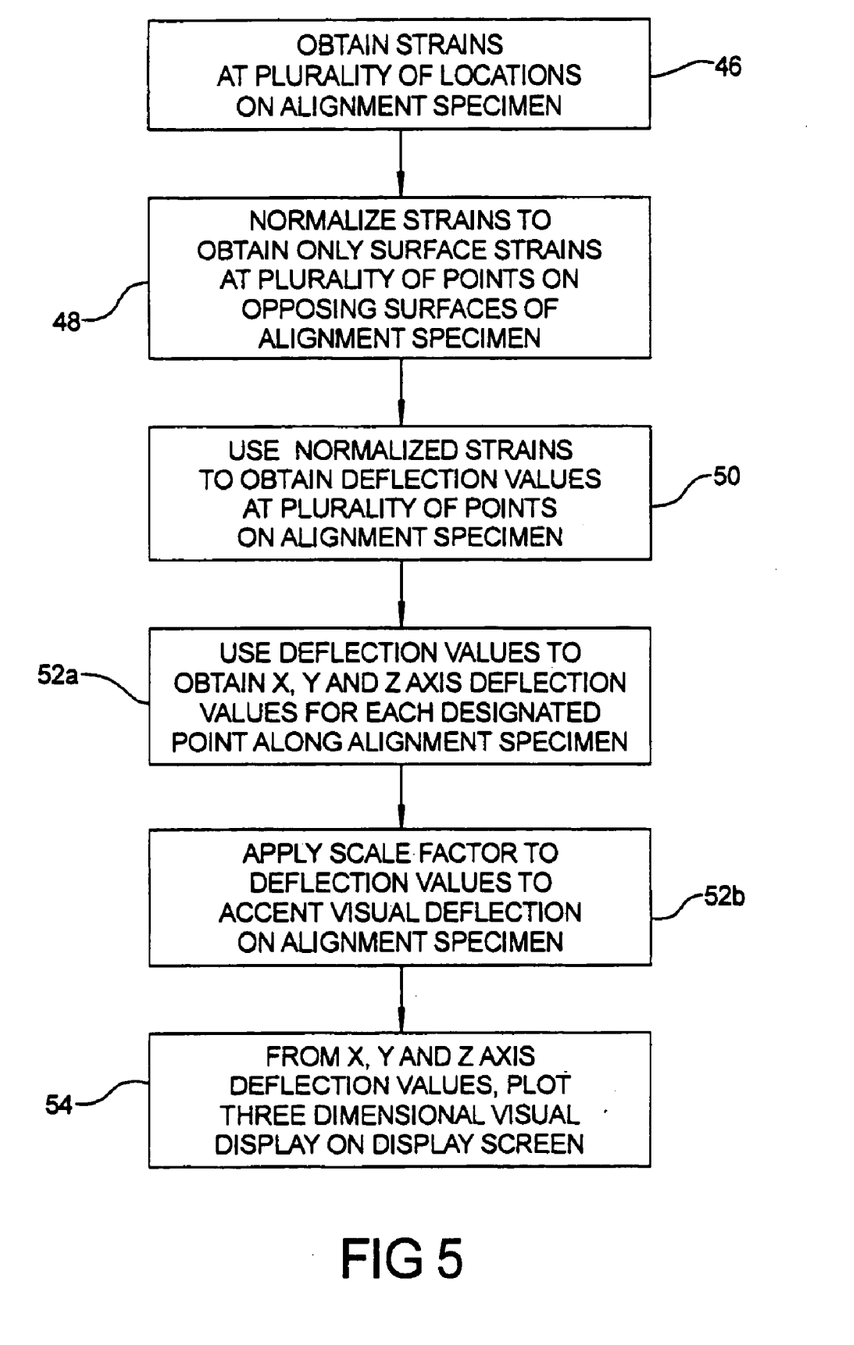
FIG. 5 is a flowchart illustrating a plurality of operations performed in implementing a preferred implementation of the present invention.

Referring now to FIGS. 4 and 5, a system and method for presenting three dimensional alignment information, in accordance with a preferred embodiment of the present invention, will be described. With initial reference to FIG. 4, a simplified drawing of the alignment specimen 32 is illustrated to aid in understanding the various formulas employed in connection with implementing the method of the present invention. The alignment specimen 32' has a thickness designated by "2y". A first pair of strain gages 38 are located at a distance "$X_1$" from the stationary end of the alignment specimen 32'. A second pair of strain gages 38 are located at a second distance "$X_2$" from the stationary end of the alignment specimen 32'. Since FIG. 4 shows a simplified version of the alignment specimen 32' the enlarged end portions 34 at the end of alignment specimen 32 have been omitted because of two assumptions:

1. the majority of the enlarged portion 34 is gripped in the load frame head (either upper head 28 or lower head 30), and therefore restrained from bending; and 2. the end portions 34 are of sufficient thickness that bending at those areas defined by the enlarged ends 34 is significantly less than bending in the central portion 36 of the alignment specimen 32.

The bending in an alignment specimen can be represented as a cantilever beam held at one end, while loads are applied to the other end. The stationary end represents the upper head of the load frame which is immoveable with respect to the frame. The load M and P applied to the other end of the specimen represent the loads applied by the lower head when the system is out of alignment. When the system is perfectly aligned M and P will both be zero and no bending will occur in the specimen.

The load case presented in FIG. 4 is a complex load case represented by the following equations:

$$\delta = \frac{PX^2(3L-X) + 3MX^2}{6EI} \quad (1)$$

$$\sigma = \frac{M + P(L-X)Y}{I} \quad (2)$$

where δ is the deflection away from zero (in the +/−y direction) at any position x along the length of the specimen, L is the length of the specimen, P is the Load from FIG. 4, M is the moment from FIG. 4, E is the modulus of elasticity of the material the specimen is constructed of, I is the cross-sectional moment of inertia of the specimen and σ is the surface stress at point x. It must be assumed that the width, height and cross-section of the specimen is constant along the entire length L, thus the moment of inertia is a constant I for the entire specimen.

The strain at four points' $\epsilon_{1u}$, $\epsilon_{1l}$, $\epsilon_{2u}$, and $\epsilon_{2l}$ as shown in FIG. 4 can be calculated directly from the strains measured on the alignment specimen 32'. These strains will be normalized by the calculated average axial stress due to loading by the load frame 10, resulting in the strains $\epsilon_{1u}$, $\epsilon_{1l}$, $\epsilon_{2u}$ and $\epsilon_{2l}$ representing only the surface strain due to misalignment of the upper head of the load frame. The subscript letter $_u$ will be used to arbitrarily designate one side of the specimen, and the subscript letter $_l$ the other side.

Using equations (1) and (2) and basic mechanics of materials relating to stress analysis, the following equations can be derived for the bending case of the alignment specimen 32':

For the upper (u) side:

$$\delta_u(X) = \frac{X^2((\varepsilon_{1u} - \varepsilon_{2u})X - 3(\varepsilon_{1u}X_1 - \varepsilon_{2u}X_2))}{6(X_1 - X_2)Y} \quad (3)$$

$$M_u = \frac{EI(L(\varepsilon_{1u} - \varepsilon_{2u}) - \varepsilon_{1u}X_2 + \varepsilon_{2u}X_1)}{(X_1 - X_2)Y} \quad (4)$$

$$P_u = \frac{-EI(\varepsilon_{1u} - \varepsilon_{2u})}{(X_1 - X_2)Y} \quad (5)$$

For the (l) lower side:

$$\delta_l(X) = \frac{X^2((\varepsilon_{1l} - \varepsilon_{2l})X - 3(\varepsilon_{1l}X_1 - \varepsilon_{2l}X_2))}{6(X_1 - X_2)Y} \quad (6)$$

$$M_l = \frac{EI(L(\varepsilon_{1l} - \varepsilon_{2l}) - \varepsilon_{1l}X_2 + \varepsilon_{2l}X_1)}{(X_1 - X_2)Y} \quad (7)$$

$$P_l = \frac{-EI(\varepsilon_{1l} - \varepsilon_{2l})}{(X_1 - X_2)Y} \quad (8)$$

Because the alignment specimen is assumed to be symmetrical across the loading axis, the values of $\delta_l$ and $\delta_u$ will be exactly opposite, while $M_l$ and $M_u$, and $P_l$ and $P_u$ will be identical, within the error introduced to the system from the error in measurement in the strain gages 38.

Three-dimensional Display

Equations (3) and (6) are used directly to create the three-dimensional display because they represent the deflection of the alignment specimen 32 away from the load axis. Three matrices are constructed such that they define a three dimensional surface and two dimensional projections of this surface. This surface, when graphed using a parametric plot, shows a three-dimensional representation of the specimen, including any bending that occurs due to sensed misalignment at those locations where the strain gages 38 are located. The projections of the surface help to emphasize the misalignment of the end user. The matrices are expressed as follows:

$X(1,x) = S^*(\delta_l(x) + y)$ $X(2,x) = S^*(\delta_u(x) - y)$ $X(3,x) = S^*(\delta_u(x) - y)$ $X(4,x) = S^*(\delta_l(x) + y)$ $Y(1,x) = -w/2$ $Y(2,x) = -w/2$ $Y(3,x) = w/2$ $Y(4,x) = w/2$ $Z(1,x) = x$ $Z(2,x) = x$ $Z(3,x) = x$ $Z(4,x) = x$ The term "X" is the parametric x-axis positions, "Y" is the parametric y-axis positions and "Z" is the parametric z-axis positions for all numbers x. The term "S" is a user selectable scale factor which modifies the visualization of the deflection to create a more pronounced (i.e., exaggerated) deflection effect for the user. The projections are made by setting each value of a given axis to zero. For example, for a X-Z projection, X would all be zeros. For a Y-Z projection, Y would be all zeros, and for a X-Y projection Z would be all zeros.

As the strains measured from the specimen change, the values of $\delta_l(x)$ and $\delta_u(x)$ change, thus changing the parametric plot to represent the current bending condition.

With reference to FIG. 5, the operation of one preferred implementation of the method will be outlined. In operation 46, strain information is obtained at a plurality of locations on the alignment specimen 32', as provided by the strain gages 38. In operation 48, the strains are normalized to obtain only surface strain information at a designated plurality of points on opposing surfaces of the alignment specimen 32'.

In operation 50, the normalized strains are used to obtain deflection values at the designated plurality of points on the alignment specimen 32'. In operation 52a, the deflection values obtained in operation 50 are then used to obtain X, Y and Z axis deflection values for each of the designated points along the alignment specimen 32. At operation 54b, a scale factor (e.g., 5, 10, 100, etc.) is applied to the deflector values. This provides a three dimensional representation of the deflection of the alignment specimen at each of the given designated points that is slightly exaggerated to enable an operator to more readily visualize the deformation affecting the alignment specimen. In operation 54, X, Y and Z axis deflection values for each of the designated points that were determined in operation 52b are used in plotting a three dimensional visual representation of the alignment specimen on a display, such as monitor 16 (FIG. 1). The three dimensional display of the alignment specimen includes a slightly exaggerated representation of the deformation of its shape caused by the misalignment forces. Being able to readily see a deformed representation of the alignment specimen 32 enables an operator to more quickly, easily and more intuitively apply adjustments to the adjustment screws on the alignment fixture 24 of the load frame 10.

Figure 6:
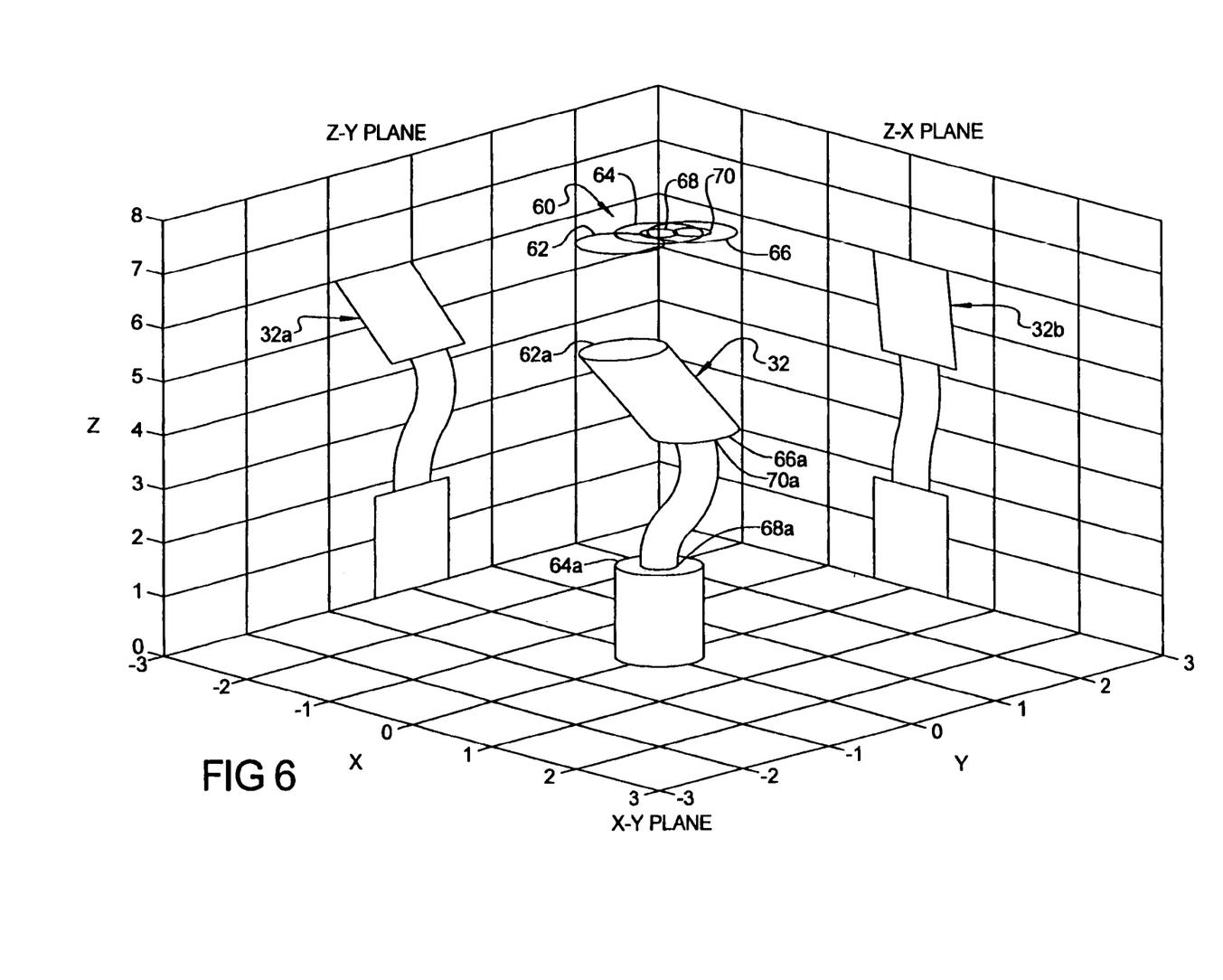
FIG. 6 is an illustration of the three dimensional image of the alignment specimen showing its deformed shape caused by misalignment forces.

A representation of the deformation of the alignment specimen 32 is illustrated in FIG. 6. FIG. 6 also illustrates a two dimensional projection 32a in a Z-Y plane 56 and, a two dimensional projection 32b in a Z-X plane 58. Projection 32a represents the deformation obtained by setting the X-axis deformation values in the foregoing formulas to zero.

Projection 32b represents the deformation obtained by setting the Y-axis deformation values to zero. Optionally, an additional three dimensional projection 60 could be provided to illustrate the relative lateral displacements of various portions of the alignment specimen 32 in only the X-Y plane. In this example, circle 62 corresponds to portion 62a on the specimen 32, circle 64 corresponds to portion 64b on the specimen 32, circle 66 corresponds to portion 66a on the specimen 32, circle 68 corresponds to portion 68a on the specimen, and circle 70 corresponds to portion 70a on the specimen 70.

The system and method of the present invention thus allows an operator to more easily adjust the components of a typical load frame to remove any concentric and/or angular misalignment of the upper head relative to the lower head. By providing a three dimensional display of the alignment specimen with a slightly exaggerated representation of the deformation of the specimen, the operator can more easily and intuitively apply the needed corrections to the load frame even more quickly than with previously developed two dimensional graphical alignment systems. Since the three dimensional display is provided essentially in real time, this further expedites the process of aligning the components of the load frame.

While various preferred embodiments have been described, those skilled in the art will recognize modifications or variations which might be made without departing from the inventive concept. The examples illustrate the invention and are not intended to limit it. Therefore, the description and claims should be interpreted liberally with only such limitation as is necessary in view of the pertinent prior art.

What is claimed is:

1. A method for illustrating, in three dimensional form, a misalignment of a portion of a load frame, relative to an alignment specimen that is being held by the load frame, when the load frame is applying a load force to the alignment specimen, the method comprising:
   securing the alignment specimen at its opposite ends to a movable load portion of the load frame, and to a fixed support of the load frame, so that the alignment specimen is approximately centered about its axial center line within the load frame;
   using the movable portion to apply an axial force to the alignment specimen generally along the axial centerline of the alignment specimen;
   sensing the axial strain experienced by the alignment specimen at a plurality of longitudinally spaced apart points along the alignment specimen, that is being caused by the movable portion applying an axial force to the alignment specimen that is not directed along the axial center line of the alignment specimen;
   using the sensed axial strain to determine deflection values for longitudinal surface portions of the alignment specimen; and
   using the deflection values to create a three dimensional representation of the alignment specimen on a graphic display terminal, in which the deformation of the alignment specimen is illustrated.

2. The method of claim 1, further comprising:
   using the sensed axial strains to determine strain values representing only the surface strains imposed in the alignment specimen that are being caused by axial misalignment of the movable load bar relative to the fixed support.

3. The method of claim 2, further comprising:
   using the sensed strains to determine said deflection values at a plurality of locations along the length of the alignment specimen, from the axial center line of the alignment specimen.

4. The method of claim 3, wherein the operation of determining said deflection values comprises determining deflection values for opposing longitudinal surface portions of the alignment specimen.

5. The method of claim 3, wherein the operation of determining deflection values includes determining a cross-sectional moment of inertia of the specimen caused by the force imposed by the movable load bar.

6. The method of claim 3, wherein the operation of creating a three dimensional representation includes using said deflection values in a plurality of matrices to define three dimensional surfaces at a plurality of points along said length of said alignment specimen.

7. The method of claim 6, wherein the matrices are used to generate x-axis, y-axis and z-axis surface information at each of said plurality of points along said length of said alignment specimen.

8. The method of claim 1, further comprising using the sensed strains to generate a two-dimensional representation of the alignment specimen on the graphic display terminal.

9. A method for illustrating, in three dimensional form, a misalignment of a portion of a load frame, relative to an alignment specimen that is being held by the load frame, when the load frame is applying a load force to the alignment specimen, the method comprising:
   securing the alignment specimen at its opposite ends to a movable load head of the load frame, and to a fixed support of the load frame, so that an axial center line of the alignment specimen is centered with an axial center line of the fixed support;
   using the movable load head to apply an axial force to the alignment specimen generally along the axial centerline of the alignment specimen;
   sensing the axial strains experienced by the alignment specimen at a plurality of longitudinally spaced apart points along the alignment specimen, that is being caused by angular or concentric misalignment of the movable load head relative to the axial center line of the fixed support of the load frame;
   using said sensed strains to generate deflection values for surface portions of said alignment specimen;
   using the deflection values to generate an exaggerated three dimensional representation of the deformation of the alignment specimen caused by said angular or concentric misalignment, and
   displaying said exaggerated three dimensional representation of said alignment specimen on a visual display terminal.

10. The method of claim 9, wherein the operation of sensing the axial strains comprises determining strain values representing only the surface strains imposed in the alignment specimen that are being caused by said angular or concentric misalignment of the movable load head relative to the fixed support.

11. The method of claim 9, wherein the operation of sensing the axial strains comprises generating strain values from a plurality of strain gages secured to said alignment specimen at spaced apart locations on the alignment specimen; and using the strain values to determine said deflection values, at a plurality of locations along the length of the alignment specimen, from the axial centerline of the alignment specimen.

12. The method of claim 11, wherein the operation of generating an exaggerated three dimensional representation includes using the deflection values to create a three dimensional representation of the alignment specimen on a graphic display terminal, in which an exaggerated representation of the deformation affecting the alignment specimen, that is caused by misalignment of the load head relative to the fixed support, is displayed.

13. The method of claim 11, wherein determining the deflection of one longitudinal surface "u" of the alignment specimen, at a given point "x" along the length "L" of the alignment specimen, is calculated by the formula:

$$\delta_u(X) = \frac{X^2((\varepsilon_{1u} - \varepsilon_{2u})X - 3(\varepsilon_{1u}X_1 - \varepsilon_{2u}X_2))}{6(X_1 - X_2)Y}$$

where "ε" represents the measured strain at a given point on one longitudinal surface of the alignment specimen.

14. The method of claim 9, wherein the operation of determining said deflection values includes determining deflection values for opposing surface portions of the alignment specimen at a plurality of locations along its length.

15. The method of claim 9, wherein the deflection away from the axial center line of the load specimen at any position "s" along a length "L" of the load specimen is calculated by the formulae:

$$\delta = \frac{PX^2(3L - X) + 3MX^2}{6EI}$$

$$\sigma = \frac{M + P(L - X)Y}{I}$$

where "M" is a moment acting on the load specimen as a result of misalignment of the load head;
where "P" is a force normal to a longitudinal surface of the load specimen that is acting on the load specimen, as a result of misalignment of the load head;
where "E" is the modulus of elasticity of a material that the load specimen is formed from; and
where "I" is a cross-sectional moment of inertia of the load specimen; and
where "σ" is a surface stress at point x.

16. A method for illustrating, in three dimensional form, a misalignment of a movable load head of a load frame, relative to fixed support of the load frame, when the load frame is applying a load force to the alignment specimen, the method comprising:
  securing the alignment specimen at its opposite ends between the movable load head and the fixed support of the load frame, so that the alignment specimen is approximately centered about its axial center line within the load frame;
  using the movable load head to apply an axial force to the alignment specimen generally along the axial centerline of the alignment specimen;
  sensing the axial strain experienced by the alignment specimen at a plurality of longitudinally spaced apart points along the alignment specimen, that is being caused by one or both of:
    angular misalignment of the movable load head, relative to the fixed support; and
    concentric misalignment of an axial centerline of said load head relative to an axial centerline of said fixed support;
  using the sensed axial strains to determine strain values representing only the surface strains imposed in the alignment specimen that are being caused by axial misalignment of the movable load head relative to the fixed support;
  using the strain values to determine deflection values, at a plurality of surface locations along the length of the alignment specimen, from the axial center line of the alignment specimen; and
  using the deflection values to create a three dimensional representation of the alignment specimen on a graphic display terminal, in which an exaggerated representation of the deformation affecting the alignment specimen is displayed.

17. The method of claim 16, wherein the operation of sensing the axial strains comprises generating strain values from a plurality of strain gages secured to said alignment specimen at spaced apart longitudinal locations on the alignment specimen; and
  using the strain values to determine said deflection values, at a plurality of locations along the length of the alignment specimen, from the axial centerline of the alignment specimen.

18. The method of claim 16, wherein the deflection away from the axial center line of the load specimen, at any position "x" along a length "L" of the load specimen is calculated by the formulae:

$$\delta = \frac{PX^2(3L - X) + 3MX^2}{6EI}$$

$$\sigma = \frac{M + P(L - X)Y}{I}$$

where "M" is a moment acting on the load specimen as a result of misalignment of the load head;
where "P" is a force normal to a longitudinal surface of the load specimen that is acting on the load specimen, as a result of misalignment of the load head;
where "E" is the modulus of elasticity of a material that the load specimen is formed from; and
where "I" is a cross-sectional moment of inertia of the load specimen; and
where "σ" is a surface stress at point x.

19. The method of claim 18, wherein determining the deflection of one longitudinal surface "u" of the alignment specimen, at a given point "x" along the length "L" of the alignment specimen, is calculated by the formula:

$$\delta_u(X) = \frac{X^2((\varepsilon_{1u} - \varepsilon_{2u})X - 3(\varepsilon_{1u}X_1 - \varepsilon_{2u}X_2))}{6(X_1 - X_2)Y}$$

where "ε" represents the measured strain at a given point on one longitudinal surface of the alignment specimen.

20. A method for illustrating a misalignment of a portion of a load frame, relative to an alignment specimen that is being held by the load frame, when the load frame is applying a load force to the alignment specimen, the method comprising:

securing the alignment specimen at its opposite ends to a movable load portion of the load frame, and to a fixed support of the load frame, so that the alignment specimen is approximately centered about its axial centerline within the load frame;

using the movable portion to apply an axial force to the alignment specimen generally along the axial centerline of the alignment specimen;

sensing the axial strain experienced by the alignment specimen at a plurality of longitudinally spaced apart points along the alignment specimen, the axial strain being caused by the force from the movable portion not applying a force directly along the axial centerline of the alignment specimen;

using the sensed axial strains to generate deflection values for surface portions of the alignment specimen;

using said deflection values to generate a three dimensional graphic representation of the alignment specimen illustrating its deformation, to assist in aligning said alignment specimen along said axial centerline; and generating a two dimensional graphic representation of the alignment specimen, illustrating its deformation, adjacent said three dimensional graphic representation.

* * * * *